(12) United States Patent
Fattinger et al.

(10) Patent No.: US 8,192,697 B2
(45) Date of Patent: Jun. 5, 2012

(54) SORPTION MICRO-ARRAY

(75) Inventors: Christoph Fattinger, Blauen (CH); Peter Berndt, Basel (CH)

(73) Assignee: F. Hoffmann-La Roche AG, Basel (CH)

( * ) Notice: Subject to any disclaimer, the term of this patent is extended or adjusted under 35 U.S.C. 154(b) by 350 days.

(21) Appl. No.: 12/079,334

(22) Filed: Mar. 25, 2008

(65) Prior Publication Data
US 2008/0245970 A1 Oct. 9, 2008

(30) Foreign Application Priority Data
Mar. 28, 2007 (EP) .................... 07105148

(51) Int. Cl.
*B01L 3/00* (2006.01)
*G01N 21/01* (2006.01)
*G01N 21/51* (2006.01)
*G01N 23/10* (2006.01)
*G01N 23/12* (2006.01)

(52) U.S. Cl. ............... 422/501; 250/428; 250/432 R; 422/502

(58) Field of Classification Search ............ 422/101; 250/432 R, 432, 428
See application file for complete search history.

(56) References Cited

U.S. PATENT DOCUMENTS

| | | | | |
|---|---|---|---|---|
| 5,047,649 A * | 9/1991 | Hodgson et al. | ............ | 250/492.2 |
| 6,002,471 A * | 12/1999 | Quake | ............... | 356/73 |
| 6,647,766 B2 * | 11/2003 | Despont et al. | ............... | 73/105 |
| 6,749,814 B1 * | 6/2004 | Bergh et al. | ............... | 422/130 |
| 7,305,869 B1 * | 12/2007 | Berman et al. | ............... | 73/105 |
| 7,528,947 B2 * | 5/2009 | Banin et al. | ............... | 356/301 |
| 2004/0037750 A1 * | 2/2004 | Stimpson et al. | ............ | 422/100 |

(Continued)

FOREIGN PATENT DOCUMENTS
WO WO 2005/046859 A2 5/2005
(Continued)

OTHER PUBLICATIONS

Fritz, James et al. "Separation of Phenols by Reversed-Phase Chromatography," Anal. Chem., 1965, vol. 37, No. 8, p. 1015-1018.*

(Continued)

*Primary Examiner* — Sam P Siefke
*Assistant Examiner* — Bryan Kilpatrick
(74) *Attorney, Agent, or Firm* — Mintz Levin Cohn Ferris Glovsky and Popco, P.C.

(57) ABSTRACT

A sorption micro-array (1) for sorbing a substance off an assay sample comprises a support (11) and a plurality of sorption elements (14). The plurality of sorption elements (14) is arranged in a well defined geometry in connection with the support (11), wherein the distance between each sorption element (14) and its adjacent sorption element (14) is predefined. Since all of the sorption elements (14) are arranged at a well defined location of the sorption micro-array (1), e.g. in a row with well defined distances from each other, the output of an analysis of substances sorbed by each of the sorption elements (14) can exactly be allocated to a well defined location of an assay sample from which the substances have been sorbed. Like this, it is possible to provide an exact chemical output image of the micro-distribution of the substances of the assay sample. The sorption micro-array according to the invention allows a gentle fluidic pick up of substances essentially without impairing the substances wherein the location of the pick up on the assay sample is well defined.

6 Claims, 9 Drawing Sheets

U.S. PATENT DOCUMENTS

2005/0047962 A1* 3/2005 Laurell et al. ............. 422/100

FOREIGN PATENT DOCUMENTS

WO    WO 2006/110135 A1    10/2006

OTHER PUBLICATIONS

Society for Biomolecular Screening,. ANSI/SBS Jan. 2004: for Microplates—Footprint Dimensions, http://www.sbsonline.org: Society for Biomolecular Screening, 2004.

Society for Biomolecular Screening, ANSI/SBS Feb. 2004: for Microplates—Height Dimensions, http://www.sbsonline.org: Society for Biomolecular Screening, 2004.

Society for Biomolecular Screening, ANSI/SBS Mar. 2004: for Microplates—Bottom Outside Flange Dimensions, http://www.sbsonline.org: Society for Biomolecular Screening, 2004.

Society for Biomolecular Screening, ANSI/SBS Apr. 2004: for Microplates—Well Positions. http://www.sbsonline.org: Society for Biomolecular Screening, 2004.

P. Vettiger, et al., The "Millipede"—Nanotechnology Entering Data Storage, IEEE Transactions on Nanotechnology, vol. 1 No. 1, Mar. 2002, (pp. 39-55).

Rubakhin, et al., "Imaging mass spectrometry: fundamentals and applications to drug discovery", DDT—vol. 10, No. 12—Jun. 2005, www.drugdiscoverytoday.com (pp. 823-837).

European Search Report for Application No. EP 07105148.6 dated Sep. 28, 2007.

* cited by examiner

SORPTION MICRO-ARRAY

This application claims priority to European Patent Application No. 07105148.6, filed Mar. 28, 2007. The contents of this priority application are incorporated by reference into this specification in its entirety.

TECHNICAL FIELD

The present invention relates to a sorption micro-array and more particular to an imaging system and an imaging method.

BACKGROUND ART

In various medical, chemical, biochemical or pharmaceutical applications the analysis of the spatial distribution and the dynamic redistribution of substances, i.e. molecules, atoms, molecular complexes and the like, in an assay sample, e.g. live or fixed cells, tissues and organs, is of importance. For example, temporal and spatial (re)distribution of molecules and molecular complexes is essential for biological processes in the human or animal body, such as the development of diseases or the action of drugs. In order to gather information about the (re)distribution of a substance in an assay sample, various "chemical imaging methods" are used that generate output images on a raster scale of millimeters, micrometers or nanometers.

For example, such chemical imaging methods are optical imaging of stained tissue sections or fluorescently labelled molecules in an assay sample, positron emission tomography, auto radiography, electron microscopy, and atomic force microscopy. While all of these methods are capable of generating multidimensional pictures with resolutions on the millimeter to nanometer scale, these methods produce rather limited chemical information which is often as important as the morphology of the analysed assay sample.

Further examples of chemical imaging methods producing rich chemical information are infrared spectroscopy, Raman spectroscopy, and nuclear magnetic resonance based imaging. Although rich in chemical information, these methods usually lack sufficient sensitivity and spatial resolution for satisfyingly providing information about the temporal and spatial micro-distribution of substances in biological samples, particularly in cells, tissues and organs.

Another highly sensitive approach used for chemical imaging is imaging mass spectrometry. Various methods of imaging mass spectrometry have already been developed. Mass spectrometry is an analytical method that measures the mass-to-charge ratios of ions allowing the detection of known as well as of unknown substances. A general requirement for mass spectrometry analysis is that the substance to be analyzed has to be transferred into the gas phase and has to be ionized. This can for example be achieved by ion-beam-induced desorption, laser desorption or electrospray ionization. In imaging mass spectrometry, substances from a plurality of predefined spatial spots of an assay sample are transferred into the gas phase, ionized and then analyzed via mass spectrometry one after another. The results of the mass spectrometry analysis together with the spatial information of the spots can then be used to produce a chemical output image corresponding to the assay sample.

Some imaging mass spectrometry methods include for example ion-beam-induced desorption to perform ionization and sputtering of substances using a beam of high-energy ions. This ion beam is typically formed by means of an electric field and is impacted on the assay sample surface for inducing collisions. Thereby, some of the substances of the assay sample are ejected from the surface into the gas phase. Typically, ion-beam-induced desorption results in small fragment ions and atoms and is not suitable for imaging larger molecules, in particular biomolecules.

Other imaging mass spectrometry methods include laser desorption, where photons of a laser beam are used instead of the high-energy ions described above. Again, small fragment ions and atoms do result from laser desorption not enabling satisfying imaging of larger molecules. Particularly for imaging larger molecules, such as biomolecules, laser desorption has been further developed to matrix-assisted laser desorption ionization (MALDI). Therein, the assay sample is primarily coated by a matrix and certain substances are extracted into the matrix. Then an appropriate laser focus steps across the assay sample, typically in a raster pattern. The laser radiation is locally absorbed by the matrix leading the substances to be ionized and to be released from the matrix. Only little fragmentation of the substances occurs during this desorption process making matrix-assisted laser desorption ionization suitable for many chemical imaging applications. However, the development and selection of a matrix material suitable for desorption of a broad variety of substances is a difficult task. Additionally, the matrix is often not vertically extracting the substances out of the assay sample and horizontal diffusion of the molecules occurs inside the matrix. Finally, the volume of matrix plasma to be generated for ionization of biomolecules can not be made infinitely small, ion extraction starts only after a finite volume threshold. These effects deteriorate spatial resolution of chemical imaging methods using imaging mass spectrometry with matrix-assisted laser desorption ionization.

Still further, imaging mass spectrometry methods can also include the use of high voltage for extracting substances from the assay sample and for retaining the substances on an extractor. This use of high voltage results in fragmented molecules and is also not suitable for chemical imaging of larger molecules, in particular of biomolecules.

In addition to the described ionization methods that are used in imaging mass spectrometry, additional ionization methods are known that have not yet found application for imaging of biomaterials. These methods include electrospray ionization, where an aerosol of highly ionized droplets composed of volatile solvents and non-volatile analyte substances is formed in an electric field. The droplets are subsequently reduced in size by a combination of solvent evaporation and solvent coulombic explosions until ionized substances in gas phase result. Electrospray ionization causes only little substance fragmentation. However, for assay samples with high concentrations of inorganic salts, detergents or other non-volatile substances how they occur in tissue slices and other biomaterials mass spectrometry methods with direct electrospray ionization are not suitable.

Therefore there is a need for a device enabling an economic and exact chemical imaging of comparably large molecules, particularly biomolecules in assay samples.

DISCLOSURE OF THE INVENTION

According to the invention this need is settled by a sorption micro-array as it is defined by the features of independent claim 1, by an imaging system as it is defined by the features of claim 11 and by a method as it is defined by the features of claim 16. Preferred embodiments are subject of the dependent claims.

In particular, the invention deals with a sorption micro-array for sorbing a substance off an assay sample. It comprises a support and a plurality of sorption elements being arranged in a well defined geometry in connection with the support. The distance between each sorption element and its adjacent sorption element is predefined. The term "substance" as used herein refers to any kind of chemical and/or biological molecule or molecular entity, for example sugars, lipids, hormones, proteins, peptides and nucleic acids. Further, the term "assay sample" as used herein refers to living, chemically fixed or frozen including lyophilized organisms, tissues or cell cultures, or portions, sections and extracts thereof, including smears. Still further, the term "sorption" as well as its derivations as used herein refer to all suitable reversible non-covalent binding mechanisms for assimilating a substance in or on the sorption element.

In order to provide a robust and economically manufacturable sorption micro-array, the support can for example be made of a polymeric material, of a metallic foil or of crystalline silicon. The sorption elements are preferably made of a material suitable for sorbing substances for which the presence, the concentration and/or the distribution in the assay sample is to be detected and displayed. In particular, the sorption elements can be made of a chromatographic material and more particularly of a reverse phase chromatographic material. The shape and the size of the sorption element can be optimized to the chemophysical conditions of the substances, of the assay sample and of the sorption micro-array. For example, the sorption micro-array can be provided with comparably large sorption elements if a comparably large amount of molecules needed for detection is to be sorbed. Preferably, the sorption elements of a sorption micro-array all have the same or similar mechanical properties (e.g. height of the apex, resiliency, etc), geometric properties (e.g. shape) as well as chemical properties (e.g. absorption). The term "similar" in this context means, that under identical conditions (i.e. at the point of contact with the sample the same amount of substance is present, the sorption elements are pressed against the sample with the same force) the same amount of substance is bound to the sorption elements.

In use, the sorption micro-array can be located at a predefined position in contact with the assay sample such that the sorption elements are capable of sorbing one or a plurality of substances off the assay sample. The sorbed substances can then be qualitatively and/or quantitatively analyzed by an appropriate analyzing unit wherein the substances typically have to be preprocessed before being analyzed. For example, when sorption elements made of a chromatographic material are used, the substances may have to be eluted from the sorption elements and then the eluate may be analyzed by a suitable analyzing unit. In this context, the term "elution" as well as its derivations includes all procedures suitable for desorbing a substance or parts of it from a sorption element having sorbed the substance as described above. For the analysis various analyzing units can be used wherein depending on the substance to detect, on the assay sample and on the analysis conditions different analyzing units can be more or less suitable. For example, in a preferred embodiment, electrospray ionization mass spectrometers can be used to detect and identify substances. Other analyzing units particularly suitable for the analysis of biomolecules include for example gas chromatography-mass spectrometry devices, Fourier transform infrared devices, matrix assisted laser desorption/ionization devices, multiplexed antibody arrays, and polymerase chain reaction devices.

Since in the sorption micro-array according to the invention all of the sorption elements are arranged at a well defined location of the sorption micro-array, i.e. in a well defined geometry with well defined distances from each other, the output of the analysis of each sorption element can exactly be allocated to a well defined location of the assay sample. Like this, it is possible to provide an exact chemical output image of the micro-distribution of the substances of the assay sample. The term "output image" in this context includes all data storage or display for describing the distribution of the substances in the assay sample. For example, it includes the combination of information resulting of the analyzing unit with location information of the assay sample, such as for example the coordinates of the sorption elements on the assay sample, in a database as well as the graphical representation thereof.

Thus, the sorption micro-array according to the invention allows a gentle and localized extraction of substances from an assay sample essentially without impairing the substances and the analysis of the extracted substances in a dedicated analyzing unit where elution and analysis of the extracted substances takes place for generating a chemical image of the assay sample. Further, the micro-array according to the invention provides the possibility that the assay sample and the analyzing unit are locally separated from each other and that substances sorbed from the assay sample can be transferred to the distant analyzing unit.

In a preferred embodiment, the plurality of sorption elements is arranged in a row and the distance between each sorption element and its adjacent sorption element is predefined. Such arrangement of the sorption elements in a row provides a simple geometry allowing an easy allocation to a location of the assay sample. In a further preferred embodiment, the sorption micro-array comprises a plurality of rows of sorption elements, wherein the distance between each row and its adjacent row is predefined. Like this, it possible to more efficiently provide an output image in comparison to embodiments employing single sorption elements or single rows of sorption elements. In particular, when sorption elements made of a chromatographic material are used, the process of sorbing the substances off the assay sample or of eluting them into an eluate can be time consuming compared to the process of analyzing the substances. Therefore, it can be more efficient to perform sorption of substances at a larger plurality of locations off the assay sample in parallel.

Preferably, the distance of each sorption element and its adjacent sorption element is smaller than 100 micrometer (μm), preferably smaller than 30 μm. With such an arrangement of the sorption elements, a comparably small and compact sorption micro-array can be provided enabling an efficient provision of an output image in a suitable scale and in a suitable resolution representing the substances' micro-distribution in the assay sample. Particularly for the sorption of biomolecules, the distance is preferably smaller 100 μm, wherein depending on the particular substances, the distance is often advantageously smaller than 30 μm.

In a preferred embodiment the sorption micro-array has an essentially rectangular shape wherein its sides are smaller than 1 mm. Such a sorption micro-array enables a comparably compact arrangement of the sorption micro-array having a sufficient amount of sorption elements for an efficient sorption of substances in a satisfying resolution.

In a preferred embodiment the sorption micro-array further comprises a plurality of cantilevers each having a first longitudinal end region and a second longitudinal end region, wherein each of the first end regions is connected to the support and each of the second end regions is connected to one of the sorption elements. Such cantilevers provide an elastic interconnection between the sorption elements and the support allowing compensation of possible unevenness of the assay sample as well as a slight pushing of the sorption elements, i.e. an application of a small force on the sorption elements, onto the assay sample while sorbing the substances.

Further, the sorption micro-array preferably comprises a plurality of tips being connected to the support wherein each sorption element is arranged at an apex of one of the tips. With sorption elements being arranged on the apexes of tips, the sorption element is silhouetted against the support such that contact between the sorption elements and the assay sample can easily be provided. When the sorption micro-array comprises cantilevers as described above, each tip is arranged at the second longitudinal end region of one of the cantilevers. This additionally eases the compensation of possible unevenness of the assay sample as well as the slight pushing of the sorption elements onto the assay sample.

In one preferred embodiment, each tip has a longitudinal channel in which one of the sorption elements is arranged overlapping the apex of its respective tip. In such an arrangement, the sorption elements can be directly connected to elution means via the channels, such that sorbed substances can be eluted from each sorption element through its encompassing channel. Further, each sorption element can have a comparably big volume allowing the sorption of comparably large amounts of substances and/or of comparably large substances. Particularly, when the sorption micro-array is used for the imaging of the micro-distribution of biomolecules in assay samples, a certain minimum amount of biomolecules has to be sorbed in a single sorption element in order that the analyzing unit is capable of detecting it. When using state-of-the-art analyzing units, such as for example mass spectrometry, a minimum amount of about 100 attomole of biomolecules has to be present in a picoliter to be detectable.

Each sorption element can have a pointed shape projecting away from the support. With such a pointed shape, the assay sample can be pierced. For example, when the assay sample comprises cells, the membranes of the cells can be pierced such that the interior of the cells can be reached by the sorption micro-array. The sorption elements can be arranged in according longitudinal channels inside the tips as described above as well as in any other suitable manner.

In a second preferred embodiment, each sorption element has a shape of a globule with a diameter of less than 50 µm, preferably less than 20 µm and more preferably less than 2 µm. With such an arrangement of the sorption elements a comparably small, i.e. up to nanometer scale, and compact sorption micro-array can be provided wherein each sorption element has a sufficient binding capacity for the detection of the substances in a suitable analyzing unit. In order to achieve an as efficient sorption as possible with an as high resolution as possible, the diameters of the globule are in the above mentioned ranges depending on the kind of biomolecules to be sorbed. Further, such globule shaped sorption elements are easily manufacturable.

Preferably the sorption micro-array is colorized such that each of the sorption elements is heatable by a light beam or infrared radiation. For example the surface of the support averted to the sorption elements or spots on that surface being adjacent to the sorption elements can be colorized with a dark color, in particular with black. When a light beam or infrared radiation is pointed to said spots the support and the adjacent sorption elements can be heated. Particularly when frozen assay samples are used, such as for example frozen tissue section assay samples, small areas of the assay sample can be defrosted while sorbing the substances. Since sorption processes are more efficient in liquid phase than in frozen phase, such a colorized sorption micro-array enables a more efficient sorption of the substances. Moreover, it enables only to defrost small areas of the assay sample being in contact with sorption elements and keeping the rest of the assay sample in a frozen state. Like this, longitudinal diffusion can be prevented and high resolution imaging can be enabled.

A second aspect of the invention deals with an imaging system comprising the sorption micro-array described above. The imaging system further comprises a micro-fluidic chip having a fluid channel being passable by an eluent, and an elution sink for accommodating one of the sorption elements in connection with the fluid channel. The eluent can be any fluid including liquids as well as gases being suitable for the elution of the substances off the sorption elements. As described hereinbelow, the combination of the sorption micro-array and the micro-fluidic chip in an imaging system allows a convenient and efficient imaging of an assay sample.

Using the imaging system according to the invention, one or several substances can be sorbed off an assay sample by means of the sorption micro-array described above. After this sorption, the sorption micro-array can be relocated and positioned at the micro-fluidic chip such that one of the sorption elements is accommodated in the elution sink. The eluent can then be passed through the fluid channel and through the elution sink. If substances have been sorbed by the sorption element being accommodated in the elution sink, they can be eluted off the sorption element by the eluent. The eluate can then be passed into an analyzing unit where it can be analyzed. The result data of this analysis together with information of the position on the assay sample can then be stored to create an output image. In further steps, one sorption element after another can be accommodated in the elution sink and be eluted until all sorption elements of the sorption micro-array have been eluted. The sorption micro-array can then again be positioned in contact with the assay sample on a different predefined location and after sorption it can again be relocated to the micro-fluidic chip. As it is obvious to a person skilled in the art, the sorption micro-array can as well be regenerated prior of being positioned again in contact with the assay sample or it can be used just once and then be disposed. The steps of sorption, elution and analysis can be repeated until an output image of a preferred scale and of a preferred resolution is achieved.

Preferably, the micro-fluidic chip further comprises a valve being arranged at the fluid channel upstream of the elution sink for controlling the eluent passing the elution sink. With such a valve the passing of the eluent through the fluid channel and the elution sink can easily be controlled. For example, the valve can be opened for certain time while one of the sorption elements is accommodated in the elution sink. This allows for example to be sufficiently clear at any time which sorption element is eluted and which eluate is analyzed.

Preferably, the micro-fluidic chip further comprises a heater for heating the elution sink. With such a heater the temperature for performing the elution while one of the sorption elements is accommodated in the elution sink can be optimized such that an improved elution is possible.

In a preferred embodiment, the micro-fluidic chip has a plurality of fluid channels and a plurality of elution sinks being arranged for accommodating the sorption elements of one row of the sorption elements at once. With such an arrangement the sorption elements of the sorption micro-array can be eluted without relocating the sorption micro-array after the elution of every single sorption element. This enables a more efficient elution of all of the sorption elements of the sorption micro-array.

Preferably the micro-fluidic chip further comprises voids for accommodating all other sorption elements not being accommodated in an elution sink when at least one of the sorption elements is accommodated in the elution sink. With such an arrangement the sorption elements not being accommodated in an elution sink can be held in organized and protected fashion.

A third aspect of the invention deals with a method for imaging the distribution of at least one substance in an assay sample using the imaging system described above. The method comprises the steps of
(a) positioning the sorption micro-array in contact with the assay sample at a predefined position;
(b) sorbing the at least one substance off the assay sample in the sorption elements of the sorption micro-array;
(c) relocating the sorption micro-array from the assay sample and positioning it at the micro-fluidic chip such that at least one sorption element is accommodated in at least one elution sink of the micro-fluidic chip;
(d) eluting the at least one substance off the at least one sorption element being accommodated in the at least one elution sink;
(e) passing the eluate into an analyzing unit for the analysis of the at least one substance;
(f) gathering the analyzing results for providing an output image representing the assay sample;
(g) repeating steps (c) to (f) with the next at least one sorption element of the sorption micro-array until each of the sorption elements of the sorption micro-array has been accommodated in the at least one elution sink; and
(f) repeating steps (a) to (g) with changing predefined positions until the output image has a predefined scale and a predefined resolution.

With such a method an efficient provision of an output image representing the micro-distribution of a substance in an assay sample is possible.

Preferably, the at least one fluid channel together with its corresponding at least one elution sink of the micro-fluidic chip is already filled with eluent while the at least one sorption element is accommodated in the at least one elution sink (step (c)). For passing the eluent into an analyzing unit, the micro-fluidic chip can be directly connected to the analyzing unit. Alternatively, the eluent comprising the at least one substance can also primarily be passed into a transfer and/or storage device, such as for example a multi-well micro-plate and then later be analyzed. In particular the multi-well microplate can be a standardized multi-well microplate arranged according to the standards developed by the Society for Biomolecular Screening (SBS) and approved by the American National Standards Institute (ANSI) [see Society for Biomolecular Screening. ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions and ANSI/SBS 4-2004: Microplates—Well Positions. http://www.sbsonline.org: Society for Biomolecular Screening, 2004.]. When an appropriate micro-fluidic chip is used, it is also possible to accommodate all sorption element of the sorption micro-array in the elution sinks of the micro-fluidic chip at once, such that steps (c) to (f) do only have to be performed once and do not have to be repeated.

In a preferred embodiment the assay sample is present in a frozen section and each of the sorption elements is heated, preferably by a light beam or infrared radiation, while sorbing the at least one substance off the assay sample in the sorption elements of the sorption micro-array. For implementing this method, a colorized sorption micro-array as described above is preferably used. Like this small spots of the assay sample can be defrosted being sufficient in size to allow the sorption of substances by means of single sorption elements. The other entire assay sample can be kept in a frozen and stable stage such that the assay sample is only affected where sorption is performed. Like this, the imaging can be precise and unadulterated.

BRIEF DESCRIPTION OF THE DRAWINGS

The sorption micro-array according to the invention, the imaging system according to the invention and the method according to the invention are described in more detail hereinbelow by way of exemplary embodiments and with reference to the attached drawings, wherein.

MODE(S) FOR CARRYING OUT THE INVENTION

In the following description certain terms are used for reasons of convenience and are not to be interpreted as limiting. The terms "right", "left", "upward" and "on top" refer to directions in the figures. The terminology comprises the explicitly mentioned terms as well as their derivations and terms with a similar meaning.

Figure 1:
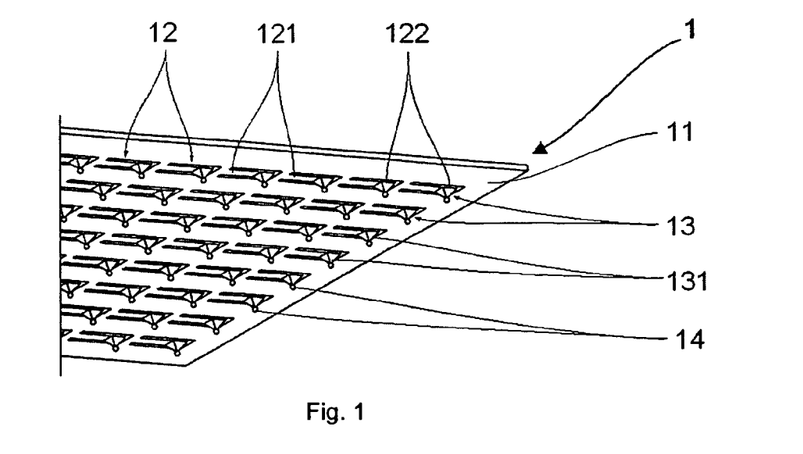
FIG. 1 shows a perspective view of a section of a schematic sorption micro-array according to the invention of a first embodiment of an imaging system according to the invention.

In FIG. 1 a sorption micro-array 1 is shown comprising a support 11 and a plurality of cantilevers 12. At its first longitudinal end region 121, each of the cantilevers 12 passes into the support 11. At a second longitudinal end region 122 of each of the cantilevers 12 a pyramidal tip 13 having an apex 131 is arranged. Further, at the apex 131 of each of the tips 13 a sorption element 14 having the shape of a globule is arranged.

The following applies to the rest of this description. If, in order to clarify the drawings, a figure contains reference signs which are not explained in the directly associated part of the description, then it is referred to previous description parts.

Figure 2:
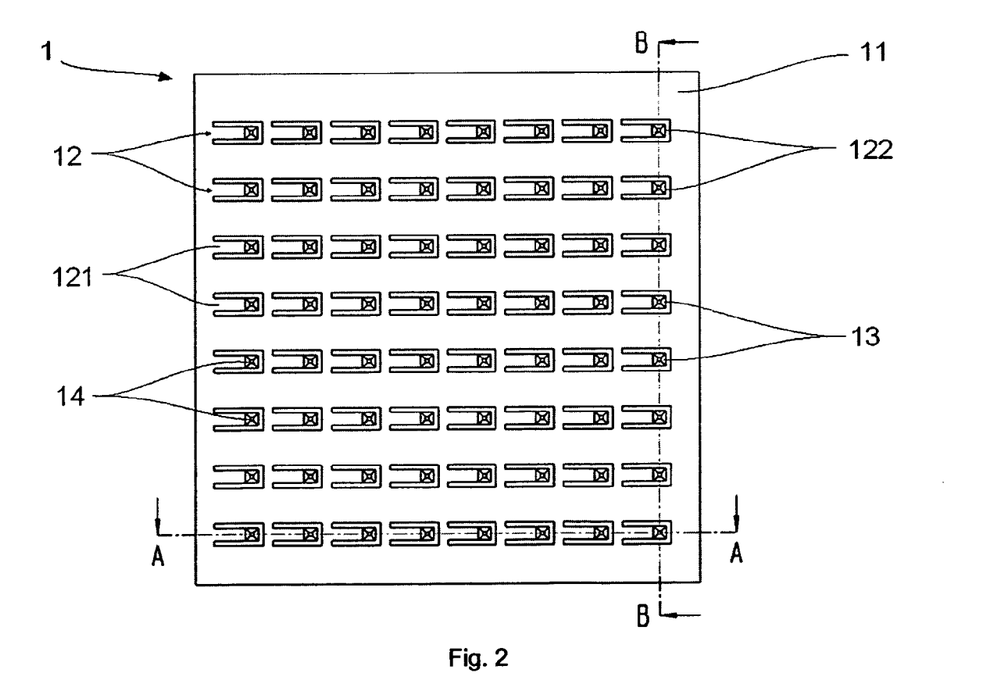
FIG. 2 shows a top view of the sorption micro-array from FIG. 1.

As best seen in FIG. 2, the sorption micro-array 1 has the shape of a square and comprises sixty-four sorption elements 14 being arranged in eight parallel rows. Each row contains eight sorption elements 14 wherein the distance between each sorption element 14 and its adjacent sorption element 14 is predefined. The distance between each row and its adjacent row is equal to the distance between the sorption elements 14. As best seen in FIG. 2 together with FIG. 3, the cantilevers 12 and the support 11 are made of one single squared flat piece wherein each cantilever 12 is built by arranging three slots through the piece together forming the two length sides and one width side of a rectangle. The piece can be of any suitable material such as for example a polymeric material, a metal foil or silicone.

Figure 3:
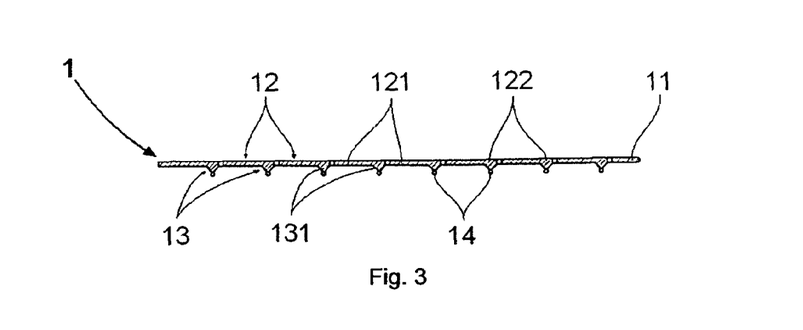
FIG. 3 shows a cross section view along the line A-A of the sorption micro-array from FIG. 2.

Each cantilever 12 is arranged parallel to its adjacent cantilever 12 in one direction and in line with its adjacent cantilever 12 in the other direction such that the second end region 122 of all of the cantilevers 12 are at the right end of the cantilevers 12 and the first end region 121 of all of the cantilevers 12 are at the left end of the cantilevers 12. At the second end region 122 of each of the cantilevers 12 one of the tips 13 is arranged, wherein the tips 13 are again made of the single piece mentioned above.

Figure 4:
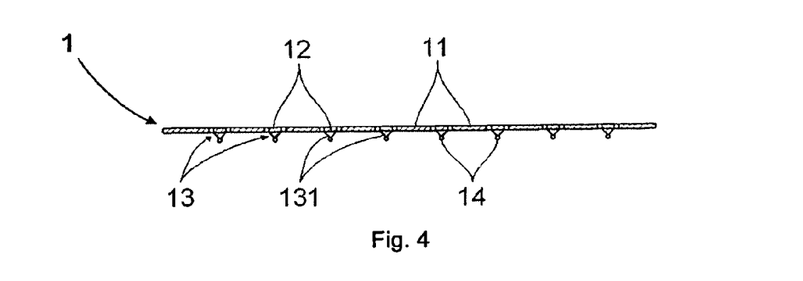
FIG. 4 shows a cross section view along the line B-B of the sorption micro-array from FIG. 2.

FIG. 4 shows one row of sorption elements 14. The sorption elements 14 have the shape of globules wherein they can be made of any suitable sorption material such as for example a chromatographic material and particularly a reverse phase chromatographic material.

Figure 5:
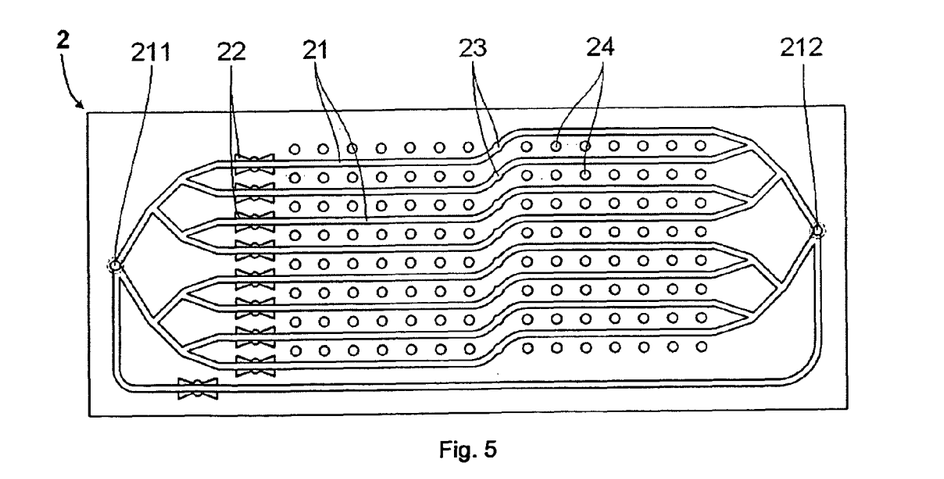
FIG. 5 shows a top view of a micro-fluidic chip of the imaging system from FIG. 1.
Figure 6:
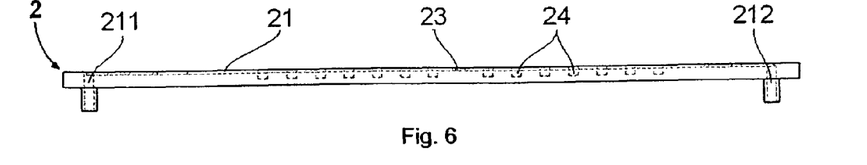
FIG. 6 shows a side view of the micro-fluidic chip from FIG. 5.

FIG. 5 and FIG. 6 show a micro-fluidic chip 2 having nine fluid channels 21 which all start at one single inlet 211 and which all end at one single outlet 212. Eight of the fluid channels 21 are arranged essentially parallel to each other wherein each of them passes an elution sink 23 such that the eight elution sinks 23 lie in a row. At each of the fluid channels 21 a valve 22 is arranged upstream from the corresponding elution sink 23, respectively, between the inlet 211 and outlet 212 of the ninth fluid channel 21 not passing one of the elution sinks 23. Further, seven rows of according eight voids 24 are arranged at the left side of the row of the elution sinks 23 as well as seven rows of according eight voids 24 are arranged at the right side of the row of the elution sinks 23.

In use, a fluid can be passed into the fluid channels 21 via the inlet 211. Depending on the state of the valves 22 the fluid is either blocked inside the fluid channels 21 or it can be passed through the corresponding fluid channels 21 out of the micro-fluidic chip 2 via the outlet 212. The fluid channels 21 are open in an upward direction. Since the diameter of the fluid channels 21 usually is very small, for example in a μm-range, the fluid can be held inside the fluid channels 21 by means of capillary forces. Thus, depending on the properties of the fluid used in the micro-fluidic chip 2, the fluid can not unintentionally escape the fluid channels 21.

Figure 7:
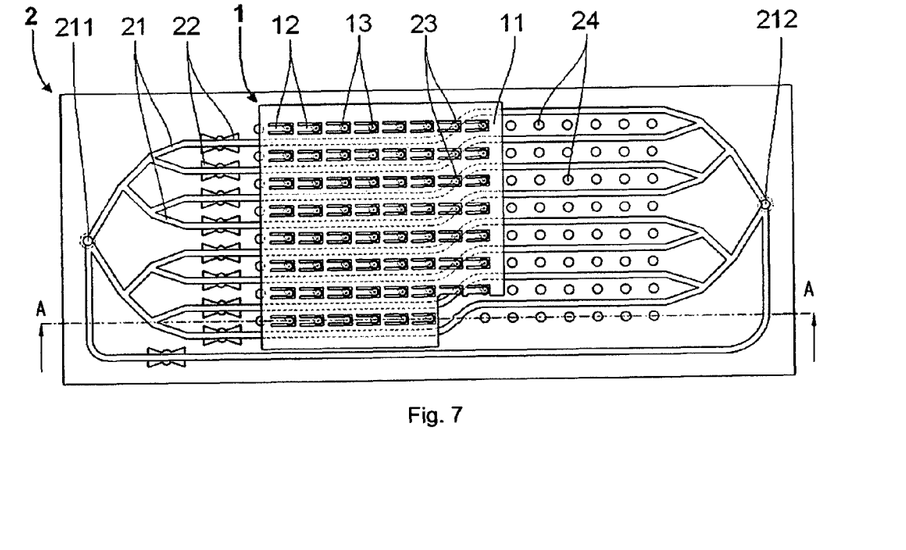
FIG. 7 shows a top view of the sorption micro-array and the micro-fluidic chip of the imaging system from FIG. 1 wherein one corner of the sorption micro-array is cut off.
Figure 8:
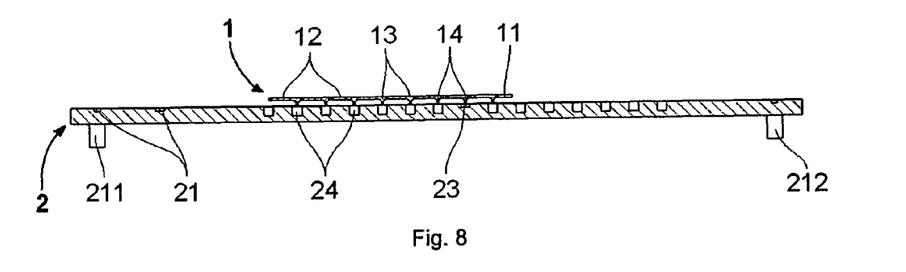
FIG. 8 shows a cross section view along the line A-A of the imaging system from FIG. 7.
Figure 9:
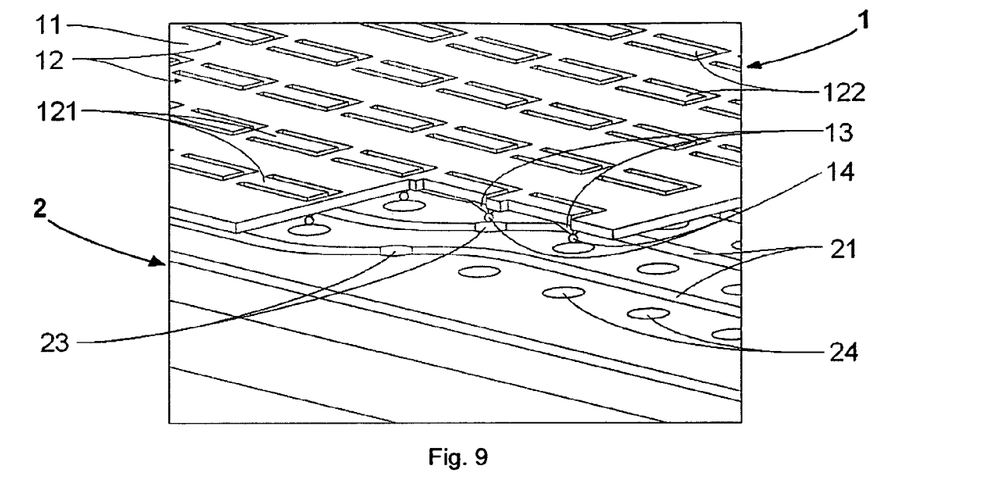
FIG. 9 shows a perspective view of a section of the imaging system from FIG. 7.

FIG. 7, FIG. 8 and FIG. 9 show an imaging system comprising the sorption micro-array 1 described above and the micro-fluidic chip 2 described above. In use, after the sorption micro-array 1 has been brought into contact with an assay sample and has potentially sorbed a substance, the sorption micro-array 1 can be positioned such that the first row of sorption elements 14 near the front of the sorption micro-array 1 is arranged inside the row of elution sinks 23. At the same time, the other seven rows of sorption elements 14 of the sorption micro-array 1 are arranged inside the seven rows of voids 24 left from the row of elution sinks 23. In this state, a suitable fluid, i.e. an eluent, can be passed through one elution sink 23 after the other by opening and closing one valve 22 after the other. Like this the substance potentially being sorbed by the sorption elements 14 can be eluted from the sorption element 14 and the eluate can be passed via the outlet 212 into a suitable analysis device. After all sorption elements 14 of the first row of sorption elements 14 are eluted, the sorption micro-array 1 can be repositioned such that the next row of sorption elements 14 is arranged inside the row of elution sinks 23. Thereby, the first row of sorption element 14 is arranged inside the first row of voids 24 right from the row of elution sinks 23 and the other six rows of sorption element 14 are arranged inside the six rows of voids 24 left from the row of elution sinks 23. This row-wise processing of the sorption elements 14 can be continued until all sorption elements 14 are eluted.

Since the sorption elements 14 are processed sequentially one after the other in the micro-fluidic chip 2 it can always made sure which eluate of which sorption element 14 is analyzed at a time. Like this, it is possible to establish from where on the assay sample an analyzed substance has been taken, such that the analyzing result of each eluate can be allocated to a well defined position of the assay sample. Thus, it is possible to provide an exact output image of the assay sample.

Figure 10:
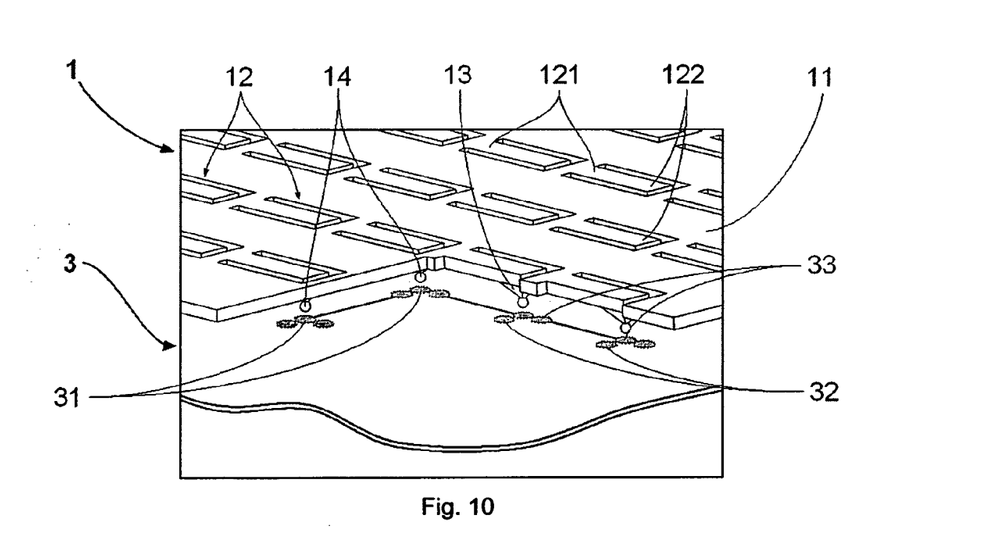
FIG. 10 shows a perspective view a section of the sorption micro-array of the imaging system from FIG. 7 interacting with a section of an assay sample in an embodiment of a method according to the invention.
Figure 11:
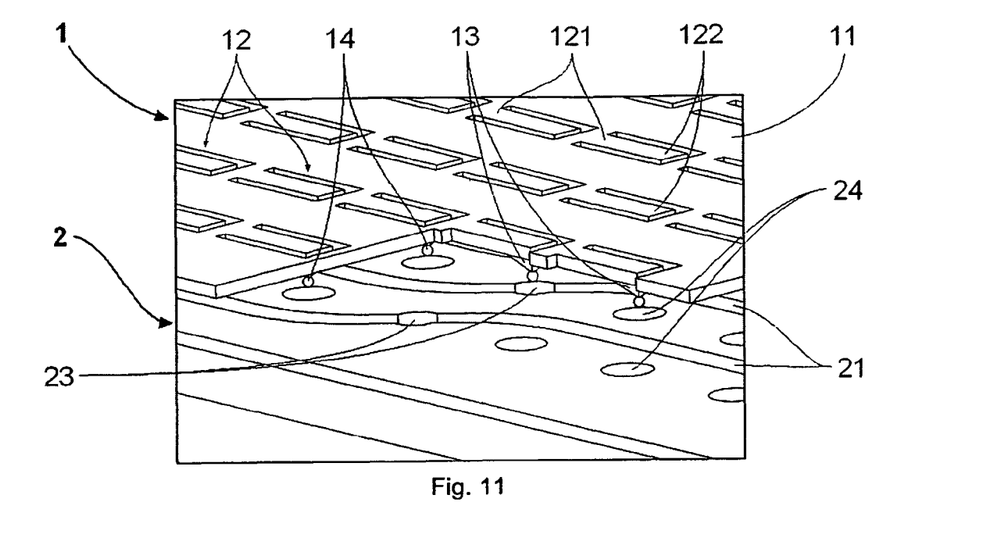
FIG. 11 shows a perspective view of the section of the sorption micro-array from FIG. 10 interacting with the micro-fluidic chip of the imaging system from FIG. 7 in the method from FIG. 10.
Figure 12:
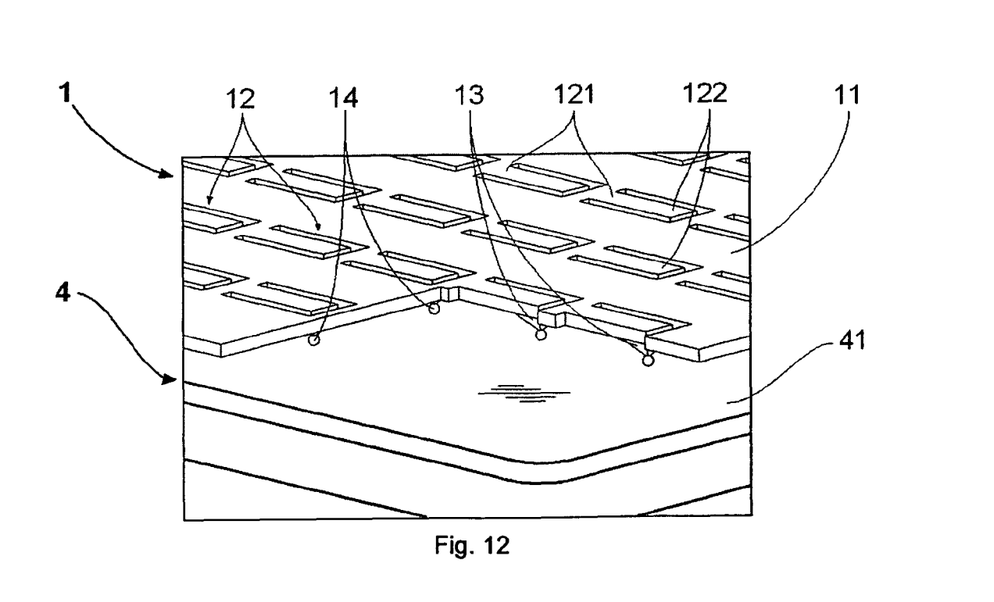
FIG. 12 shows a perspective view of the section of the sorption micro-array from FIG. 10 interacting with a regeneration unit in the method from FIG. 10.

FIG. 10, FIG. 11 and FIG. 12 illustrate a method according the invention, wherein an imaging system as described above is used. FIG. 10 shows the steps being performed in interaction with an assay sample 3, such as for example a frozen section of a tissue. The sorption micro-array 1 is arranged at a well defined position contacting the assay sample 3 at first sorption spots 31. For this positioning any suitable positioning system can be used, such as for example positioning systems known from atomic force microscopy allowing positioning at an exactness of about half of a nanometer. While contacting the assay sample 3, substances, such as for example biomolecules, being in the assay sample and being sorbable by the sorption elements 14 are sorbed off the assay sample 3 into the sorption elements 14. After sorption the sorption micro-array 1 is relocated from the assay sample 3 and positioned at the micro-fluidic chip 2. As best seen in FIG. 11, one row of sorption elements 14 is thereby accommodated in a corresponding row of elution sinks 23 of the micro-fluidic chip 2. In the meantime, the other rows of sorption elements 14 not being accommodated inside the row of elution sinks 23 are arranged inside corresponding rows of voids 24. At this stage, one valve 22 after the other is opened such that a suitable eluent passes through one elution sink 23 after the other. The substances of one sorption element 14 after the other are eluted and the corresponding eluates are passed either directly or via a transfer unit into a suitable analyzing device. After all sorption elements 14 of the sorption micro-array 1 are eluted as described above, the sorption micro-array 1 is relocated to a regeneration unit 4 having a regeneration layer 41. As shown in FIG. 12, the sorption elements 14 are held in the regeneration layer 41 until an optimized regeneration of the sorption elements 14 is performed.

After regeneration, the sorption micro-array 1 is arranged at a well defined position contacting the assay sample 3 at second sorption spots 32 and the further steps of the method are performed again as described above in a second cycle. After this second cycle the sorption micro-array 1 is arranged at a well defined position contacting the assay sample 3 at third sorption spots 33 and the further steps of the method are performed again as described above in a third cycle. In the method according to the invention as many process cycles are performed as desired for provision of an output image having a predefined scale and a predefined resolution. During the process or at a later stage, all the analyzing results of the analyzing device, such as for example qualitative and quantitative information of biomolecules, can be gathered and combined with spatial information of the assay sample 3. Like this the exact output image representing the assay sample 3 can be provided.

Figure 13:
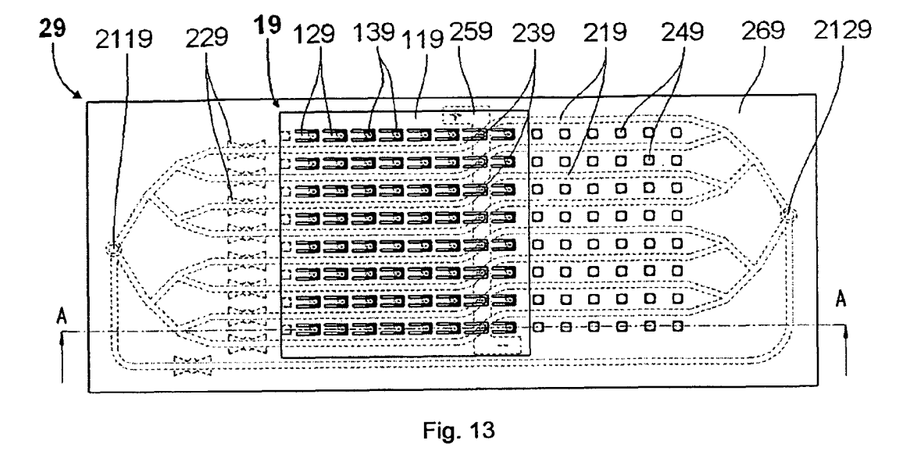
FIG. 13 shows a top view of a sorption micro-array and a micro-fluidic chip of a second embodiment of the imaging system according to the invention.
Figure 14:
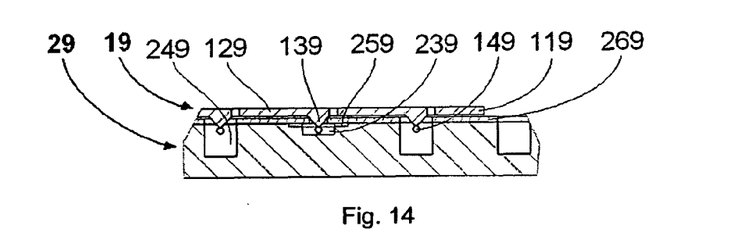
FIG. 14 shows a section around an elution sink of a cross section view along the line A-A of the imaging system from FIG. 13.

In FIG. 13 and FIG. 14 another embodiment of an imaging system according to the invention is shown. It comprises a sorption micro-array 19 with a support 119, cantilevers 129, tips 139 and sorption elements 149 arranged as in the sorption micro-array 1 described above. Further, it comprises a micro-fluidic chip 29 with fluid channels 219, an inlet 2119, an outlet 2129, valves 229, elution sinks 239 and voids 249 as the micro-fluidic chip 2 described above. The micro-fluidic chip 29 further has a resistive heater 259 arranged around the elution sinks 239. By means of this heater 259 the elution sink 239 can be heated while sorption elements 149 are arranged inside the elution sink 239 such that the elution can be processed on an elevated temperature. Elution on an elevated temperature can be significantly more efficient than on a low temperature, such that the elution of the sorption elements 149 can be performed quicker and/or more complete.

Further, a cover 269 is arranged on top of the micro-fluidic chip 29 wherein the cover 269 has through holes corresponding to the elution sinks 239 and the voids 249 of the micro-fluidic chip 29. By means of such a cover unintentional escape of fluid out of the fluid channels 219 can be prevented. This is particularly advantageous if fluid channels 219 with comparably large diameters are used, if a fluid with low capillary force properties is used and in particular if a gaseous fluid is used.

Figure 15:
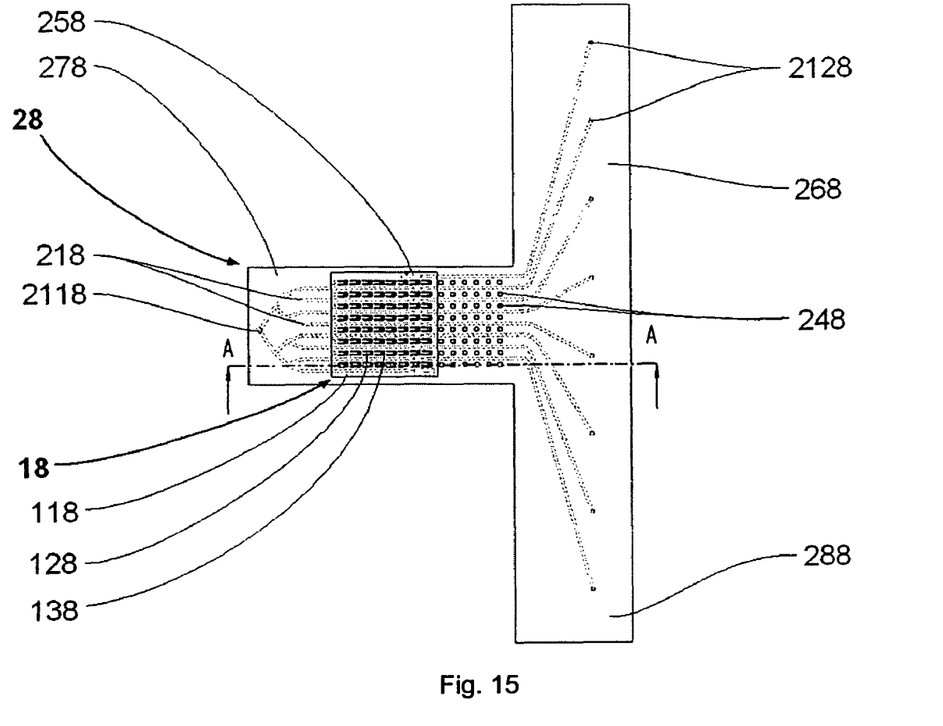
FIG. 15 shows a top view of a sorption micro-array and a micro-fluidic chip of a third embodiment of the imaging system according to the invention.
Figure 16:
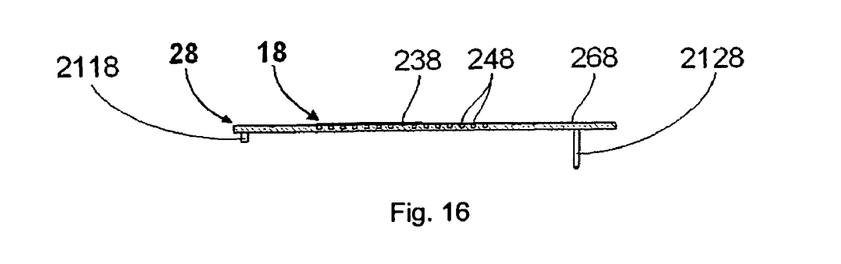
FIG. 16 shows a cross section view along the line A-A of the imaging system from FIG. 15.

In FIG. 15 and FIG. 16 a further embodiment of an imaging system according to the invention is shown. It comprises a sorption micro-array 18 with a support 118, cantilevers 128, tips 138 and sorption elements 148 arranged as the sorption micro-array 1 and as the sorption micro-array 19 described above. Further, it comprises a micro-fluidic chip 28 with fluid channels 218, an inlet 2118, elution sinks 238, voids 248, a heater 258 and a cover 268 arranged essentially as the micro-fluidic chip 29 described above. Other than the micro-fluidic chips 2 and 29, the micro-fluidic chip 28 does not comprise valves and a ninth fluid channel which is not passing one of the elution sinks 238. Further, the micro-fluidic chip 28 is T-shaped having a stem portion 278 and a cross portion 288. The inlet 2118, the elution sinks 238, the voids 248 and the heater 258 are arranged at the stem portion 278. The cross portion 288 comprises a row of eight outlets 2128 each being connected to one of the fluid channels 218.

Since the fluid channels 218 are widened up in the cross portion 288 before ending in the outlets 2128 the outlets 2128 have a comparable big distance from each other. Thus, they can easily be connected to a suitable transfer and/or storage device such as for example a multi-well microplate. In use, all sorption elements 148 of one row of the sorption elements 148 of the sorption micro-array 18 can be eluted in one step when being arranged inside the row of elution sinks 238 by passing the fluid, i.e. the eluent, through the inlet 2118 and the fluid channels 218 via the elution sinks 238. After passing the outlets 2128, the eluate can be gathered into a suitable transfer and/or storage device.

Figure 17:
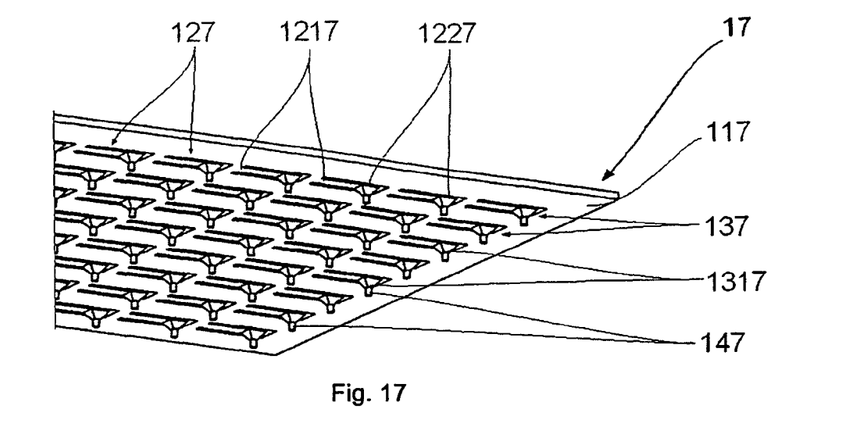
FIG. 17 shows a perspective view of a section of a further embodiment of a schematic sorption micro-array according to the invention.
Figure 18:
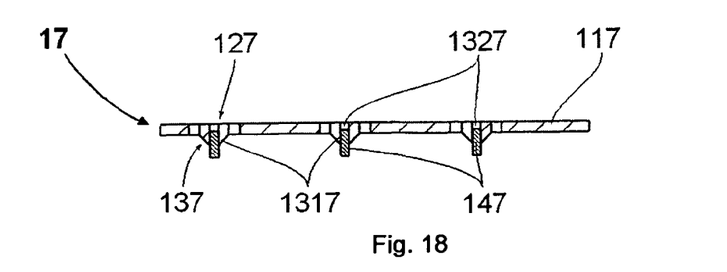
FIG. 18 shows a section of a cross section view of the sorption micro-array from FIG. 17 transverse to its cantilevers.

FIG. 17 and FIG. 18 show a further embodiment of the sorption micro-array 17 according to the invention comprising a support 117 and a plurality of cantilevers 127. At its first longitudinal end region 1217, each of the cantilevers 127 passes into the support 117. At a second longitudinal end region 1227 of each of the cantilevers 127 a pyramidal tip 137 having an apex 1317 is arranged. Each tip 137 has a channel 1327 extending through the tip 137 in its longitudinal direction. Inside each channel 1327 a cylindrical sorption element 147 is arranged overlapping the apex 1317 of its respective tip 137.

The cylindrical sorption elements 147 have a comparably large volume being capable of sorbing a comparably large amount of substances and/or of sorbing comparably large molecules. Further, the channels 1327 can be connected to an eluent source such that after having sorbed a substance the sorption elements 147 can be directly eluted via the channels 1327.

Figure 19:
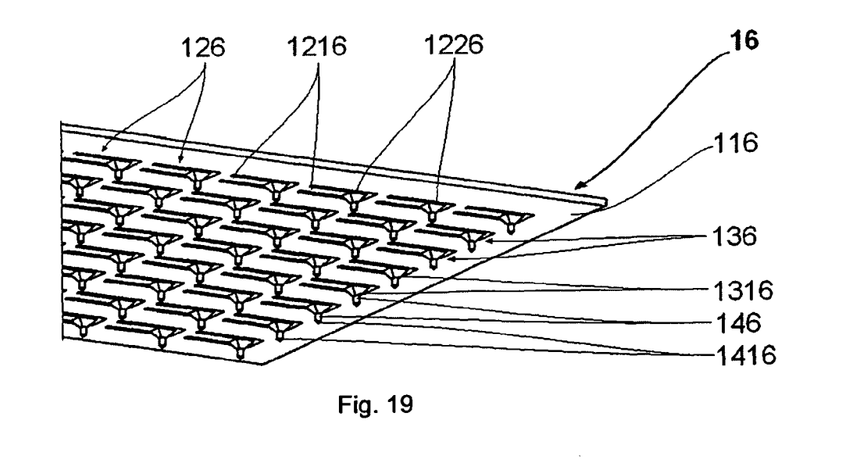
FIG. 19 shows a perspective view of a section of a another further embodiment of a schematic sorption micro-array according to the invention.
Figure 20:
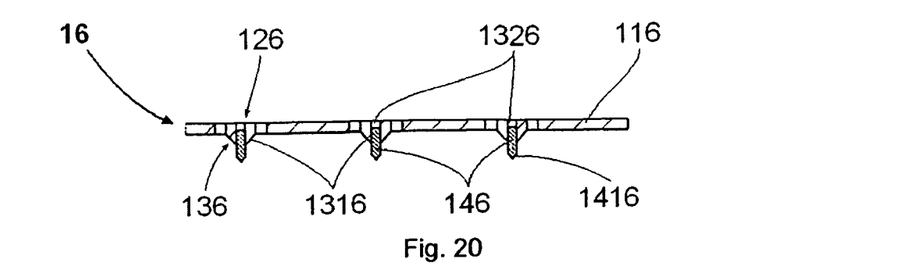
FIG. 20 shows a section of a cross section view of the sorption micro-array from FIG. 19 transverse to its cantilevers.

In FIG. 19 and FIG. 20 another further embodiment of the sorption micro-array 16 according to the invention is shown comprising a support 116 and a plurality of cantilevers 126. At its first longitudinal end region 1216, each of the cantilevers 126 passes into the support 116. At a second longitudinal end region 1226 of each of the cantilevers 126 a pyramidal tip 136 having an apex 1316 is arranged. Each tip 136 has a channel 1326 extending through the tip 136 in its longitudinal direction. Inside each channel 1326 a cylindrical sorption element 146 is arranged overlapping the apex 1316 of its respective tip 136 and having a pointed end 1416 projecting away from the support 116.

Additionally to what has been described in the embodiment of FIG. 17 and FIG. 18, the sorption elements 146 with their pointed ends 1416 can be used to pierce an assay sample. In particular, sorption elements 146 for example can be used to pierce the membrane of a biological cell assay sample for accessing the interior of the cell.

Figure 21:
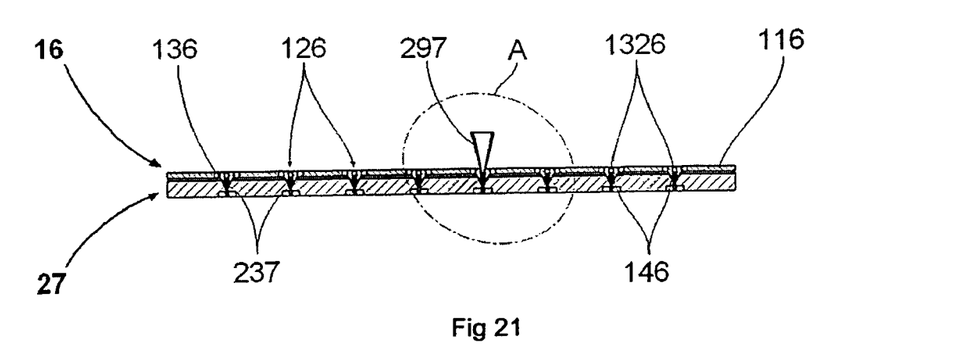
FIG. 21 shows a cross section view of the sorption micro-array from FIG. 19 transverse to its cantilevers on top of a micro-fluidic chip of a fourth embodiment of the imaging system according to the invention.
Figure 22:
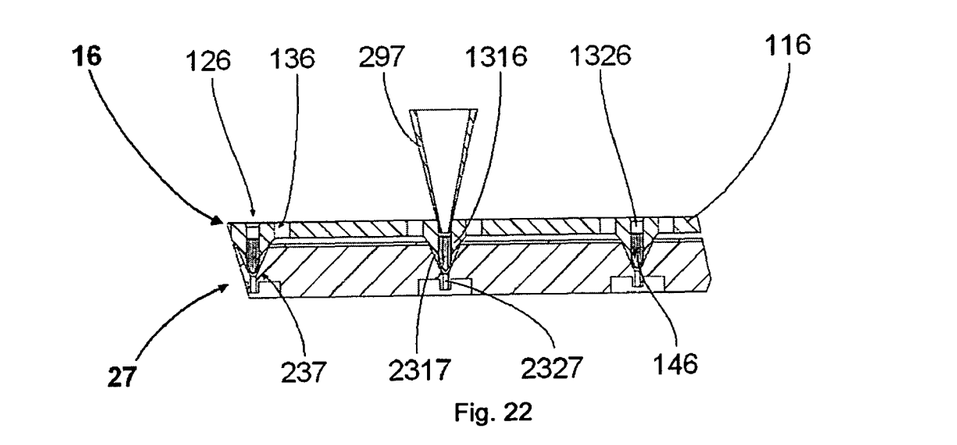
FIG. 22 shows a section of the cross section view from FIG. 21 surrounded by dotted line A.

FIG. 21 and FIG. 22 show another further embodiment of an imaging system according to the invention. The imaging system comprises the sorption micro-array 16, a micro-fluidic chip 27 and a pipette 297. The micro-fluidic chip 27 has elution sinks 237 each with an upper funnel portion 2317 being connected to a nozzle 2327 suitable for electro spray ionization mass spectrometry.

For eluting the sorption elements 146 of the sorption micro-array 16, the sorption micro-array 16 can be positioned on top of the micro-fluidic chip 27 such that the lower end of a row of the sorption elements 146 together with the lower part of the corresponding apexes 1316 is arranged inside the funnel portions 2317 of a row of elution sinks 237 of the micro-fluidic chip 27. Then, the pipette 297 is arranged in one of the channels 1326 of the row of the sorption elements 146 after another. While being inside one of the channels 1326, the pipette 297 delivers an eluent into the corresponding sorption element 146. The eluate is transferred from the sorption element 146 into the corresponding nozzle 2327 or gathered for example in a manner as described above for other embodiments of microfluidic chips. For providing advanced accessibility, upper openings of the channels 1326 are widened such that the pipette 297 can easily be introduced.

Other alternative embodiments of the sorption micro-array according to the invention, the imaging system and the method according to the invention are conceivable. Explicitly mentioned in this context are:

- The sorption micro-array can as well have another shape than the shape of a square. Additionally, another number of rows of sorption elements than eight can be arranged at the sorption micro-array wherein a row can also have another number of sorption elements than eight. In particular, the arrangement of the sorption elements can be adapted according to the transfer and/or storage device.
- The sorption elements can be arranged directly on the cantilevers or directly on the support.
- The tips can have any other suitable shape than the shape of a pyramid.
- It is also possible to arrange the apexes of the tips or even parts of the cantilevers or of the support as sorption elements.
- The arrangement of the sorption micro-array having a plurality of rows of sorption elements can be such that the distance between each row of sorption elements and its adjacent row is different from the distance between the sorption elements and their adjacent sorption elements.
- When a sorption micro-array with tips having channels is used as described above, a suitable elution device having an eluent source being connected to the channels can eluate the sorption elements directly via the channels. For example, after having sorbed substances from an assay sample, the sorption micro-array can be relocated to a gathering station and the sorption elements can be flushed by the eluent such that the substances are eluted from the sorption elements.

The invention claimed is:

1. A sorption micro-array for sorbing a substance off an assay sample, comprising a support and a plurality of sorption elements arranged in a defined geometry in connection with the support, wherein the distance between each sorption element and adjacent sorption elements is predefined, and further comprising a plurality of cantilevers each having a first longitudinal end region and a second longitudinal end region, wherein each of the first longitudinal end regions is connected to the support and wherein a tip having an apex is arranged at each of the second longitudinal end regions and a sorption element is arranged at the apex of the tip, and wherein the tip supports the sorption element;

wherein each sorption element projects at least partially from its respective tip, and wherein the sorption elements are made from a chromatographic material.

2. The sorption micro-array of claim 1, wherein each tip has a longitudinal channel in which one of the sorption elements is arranged overlapping the apex of its respective tip.

3. The sorption micro-array of claim 1, wherein each sorption element has a pointed shape projecting away from the support.

4. The sorption micro-array of claim 1, wherein each sorption element has a shape of a globule with a diameter of less than 50 μm.

5. The sorption micro-array of claim 1, colorized such that each of the sorption elements is heatable by a light beam or infrared radiation.

6. The sorption micro-array of claim 1, wherein the chromatographic material is a reverse phase chromatographic material.

* * * * *